United States Patent [19]

Kriebitzsch et al.

[11] 4,351,644

[45] Sep. 28, 1982

[54] PROCESS FOR HANDLING LIQUID CYANURIC CHLORIDE

[75] Inventors: Norbert Kriebitzsch, Hammersbach; Kurt Puschner, Frankfurt; Klaus Hentschel, Hanau, all of Fed. Rep. of Germany

[73] Assignee: Degussa Aktiengesellschaft, Frankfurt am Main, Fed. Rep. of Germany

[21] Appl. No.: 248,442

[22] Filed: Mar. 27, 1981

[30] Foreign Application Priority Data

Mar. 27, 1980 [DE] Fed. Rep. of Germany ....... 3011860

[51] Int. Cl.³ .............................................. B01J 8/08
[52] U.S. Cl. .................................. 23/293 R; 198/670; 422/232; 422/307; 423/364; 544/190
[58] Field of Search ............ 23/293 R; 422/187, 232, 422/291, 292, 307, 233; 423/364; 544/190; 198/657, 670; 126/343.5 R

[56] References Cited

U.S. PATENT DOCUMENTS

| 2,021,991 | 11/1935 | Depew | 422/232 X |
| 3,179,662 | 4/1965 | Zinsstag et al. | 544/190 |
| 3,369,873 | 2/1968 | Ullrich et al. | 23/293 R |
| 3,575,880 | 4/1971 | Wojahn et al. | 544/190 X |
| 3,607,671 | 9/1971 | Riethmann et al. | 23/293 R X |
| 4,217,451 | 8/1980 | Goedecke et al. | 544/190 |
| 4,231,755 | 11/1980 | Herzer et al. | 23/293 R |
| 4,247,240 | 1/1981 | Schora, Jr. et al. | 422/232 X |

Primary Examiner—Richard L. Chiesa
Attorney, Agent, or Firm—Cushman, Darby & Cushman

[57] ABSTRACT

Solid cyanuric chloride is supplied to the gas space of a cyanuric chloride melt with the help of a gas tight product stopper. Preferably there is used for this a screw conveyor in which the gas tight stopper is formed at the end of the screw conveyor; it is most favorable if the helix ends before the last section of the tube of the screw conveyor.

2 Claims, 1 Drawing Figure

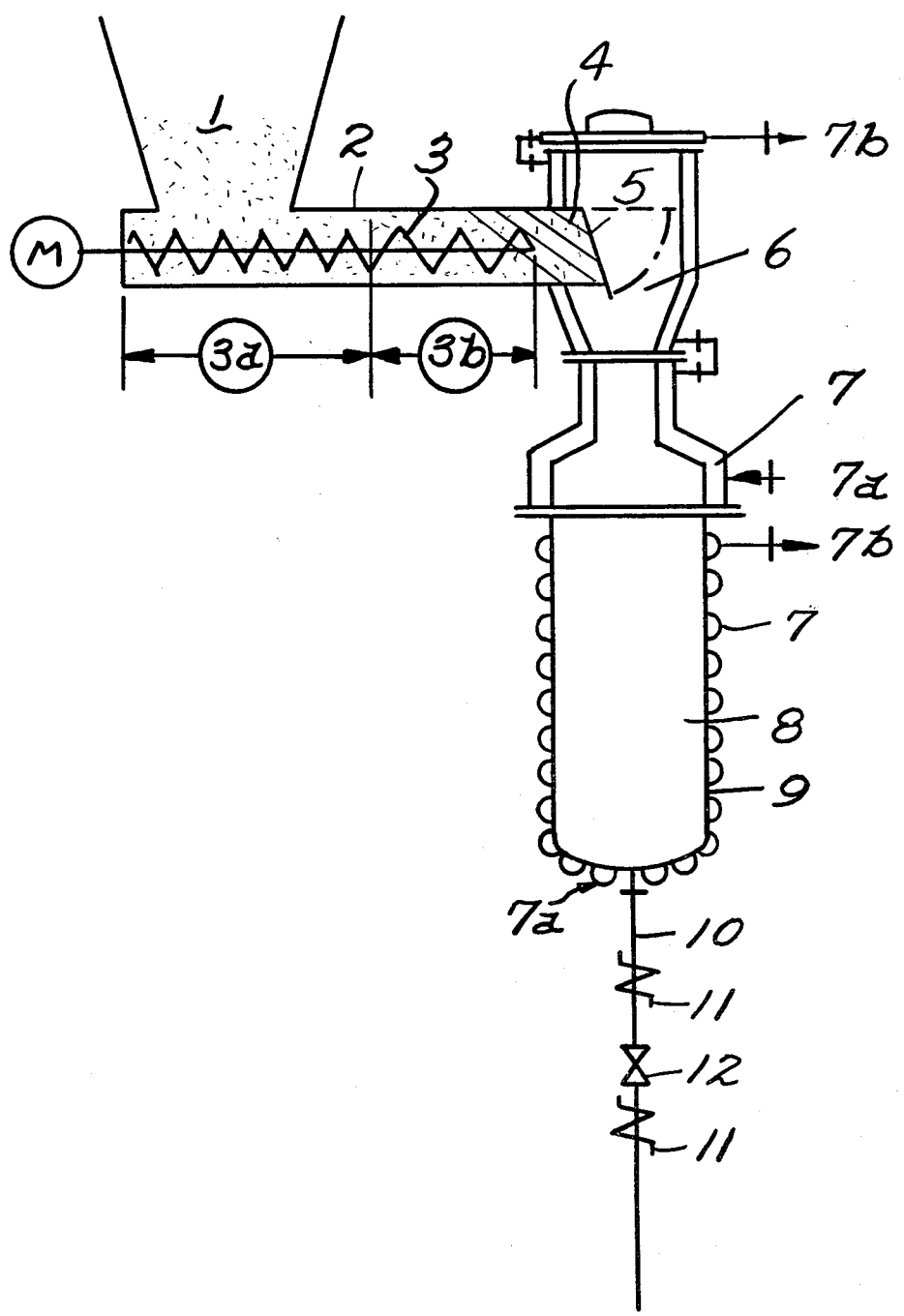

PROCESS FOR HANDLING LIQUID CYANURIC CHLORIDE

BACKGROUND OF THE INVENTION

It is known that the handling of liquid cyanuric chloride has great advantages compared to handling the solid form since the cyanuric chloride melt is transported in insulated, heatable tank cars and is stored in such types of tanks. The contact of personnel with cyanuric chloride therewith accordingly is reduced. Besides the liquid cyanuric chloride is especially suited as the starting material for continuous processes.

The only disadvantage is the very high vapor pressure which cyanuric chloride already possesses at its melting point. Through this the concentration of the cyanuric chloride in the gaseous form in the space above its melt is always relatively large.

However, difficulties can occur as a result of this if in the flow process there are formed places which are at or below the desublimation point of cyanuric chloride.

This is e.g. the case if solid cyanuric chloride is continuously introduced into the melt for melting. The introduction is always carried out in the gaseous space.

Since the solid cyanuric chloride as is understood has a lower temperature than the gas space, at the place of introduction for the solid cyanuric chloride there occurs a drop in temperature which causes a formation of crust.

Customary gas excluding supply systems for solid materials, as e.g. bucket wheel air locks, all are subject to an accretion process which lead to frequent breakdowns, above all in continuous processes using liquid cyanuric chloride.

The object of the present application is the development of a process for the easier handling in the production of liquid cyanuric chloride, preferably in continuous processes.

SUMMARY OF THE INVENTION

It has now been found that solid cyanuric chloride can be converted into cyanuric chloride melt, preferably continuously, if the particles of solid cyanuric chloride present in the vapor space above a cyanuric chloride melt are supplied through a gas tight product stopper.

The supply of the solid cyanuric chloride into the gas space can take place in simple manner with the help of a screw conveyor.

In this case it is important that the construction of the screw conveyor makes possible the formation of a gas tight stopper of the cyanuric chloride in its last tube section before entrance into the gas space.

The construction of the screw conveyor must be so designed in the product filling region that the degree of filling is as high as possible.

It is, e.g. the case with a screw conveyor whose filling region for the cyanuric chloride has a helix with a lesser pitch than in the rest of the screw conveyor tube. By the expression "in the filling region" is meant not only the region directly below the filling opening but, if it should be necessary for carrying out the invention, also the first helix in the connection to the place of filling.

By the use of different sized pitches of the helix it is possible to so compress the cyanuric chloride in the screw portion of the screw conveyor that there is formed in the last tube section before the entrance into the gas space a gas tight stopper of cyanuric chloride.

This stopping is in a position to completely seal off the screw against the gas space above the melt, so that the above-mentioned incrustations no longer can occur and it is possible to introduce the solid cyanuric chloride into the melt without friction. This is particularly essential in carrying out the process continuously. In this case the stopping always repeats in gas tight manner in continuous feeding of the solid cyanuric chloride, even if its outer end is broken off automatically after reaching the gas space.

Especially suited in a screw in which the last tube section before the entrance into the gas spaces does not contain spirals (helices).

However, there have also proven favorable screws in which there is applied a gravity type valve at the end of the tube. This can also be the case with a screw whose last tube section is free of helices.

The size of the pitches in the screw conveyors as well as the lengths of the individual tube sections belonging to the different screw conveyors are determined by preliminary experiments which have as the object the conditions for forming the gas tight stopping. Also among those conditions is the length of the last tube section in which the stopper is built.

BRIEF DESCRIPTION OF THE DRAWING

The single FIGURE of the drawings is a schematic drawing of a device in which there is represented a screw conveyor having a helix free tube section or a valve as well as two different pitches in the screw conveyor.

The process can comprise, consist essentially of or consist of the steps set forth.

DETAILED DESCRIPTION

As shown in the drawing the solid cyanuric chloride particles fall through the filling device 1, generally of commercial size, on the screw conveyor 3 which is located in the conveyor tube 2. The pitch region 3a with the small pitch of e.g. 50 mm is located in the filling region of the screw, the pitch region 3b with a pitch of e.g. 80 mm is located in the tube section after the filling region.

After passing the sections 3a and 3b, the compressed cyanuric chloride goes into the helix free tube section 4, which either can be replaced by the valve 5, which in this case is attached to the pitch region 3b, or which is additionally provided with valve 5.

Both in the helix free part 4 as well as by attachment of the valve 5 to the region 3b there are formed the gas tight stoppers. Preferably there is employed a screw conveyor having a helix free tube section.

The screw is driven by motor M.

The tube 2 of the screw projects with its last tube section into the container 9 which is divided into the melt space 8 and the gas space 6. The melting container 9 is surrounded by a heating jacket 7 in which the heating medium enters at 7a and leaves the jacket again at 7b.

As heating medium there can serve all known materials for the temperature region required, such as steam or heat carrier oils.

The melt is drawn off via line 10 having the valve 12 and the heating line 11.

EXAMPLE 1

In an apparatus according to the drawing in intervals there were conveyed 5×50 kg of cyanuric chloride within 8 minutes in each case by means of a screw 3 into a melting container 9. The length of the screw 3 was 1000 mm and the diameter 180 mm. The helices ended 200 mm before the trough discharge. The increase in pitch in the pitch section 3a was 50 mm, the increase in section 3b 80 mm. A valve 5 was not provided. The conveyor tube 2 was unheated. The solid cyanuric chloride was at room temperature. The temperature of the melt in melting container 9 was held to 170° C. (oil heating), the heating jacket 7, surrounding the vapor space 6 was heated by applied copper tubes having 10 bar steam pressure. The apparatus was de-airated into an aqueous alkaline liquor washer (not shown).

In cutting off the screw 3 the product stopper located on the screw exit acts as vapor closure for the product remaining in the screw conveyor, so that a further separatory device between solid and vapor phase is not necessary. The solid stopper of cyanuric chloride melt in the reprocessing as well as in conveying of fresh product through the screw 3 in each case permits opening again and recompressing without problem.

EXAMPLE 2

In a device as in Example 1 and in analogous manner but continuously 500 kg of cyanuric chloride were introduced into the melt present within 60 minutes and continuously withdrawn at the bottom outlet 10 of the melting container 9 at the point 13. Then the screw 3 was cut off and the heating cut off, first of the melting container 9, then of the gas space 6. The passages of the screw were then, so far as could be seen, absolutely free of coating. Near the outlet in conveyor table 2 there sat a solid product stopper, which, however, could be crushed later by the screw 3 without difficulty. The walls of the gas space 6 as well as the forward part of the conveyor tube 2 projecting into the gas space 6 were completely free of coatings.

The entire disclosure of German priority application No. P 3011860.6-44 is hereby incorporated by reference.

What is claimed is:

1. In a process of supplying and conveying solid cyanuric chloride into a cyanuric chloride melt wherein there is provided a screw conveyor having a first screw portion having a selected helix pitch and a second screw portion having a selected helix pitch that is larger than said selected helix pitch of said first portion, said screw conveyor being disposed in conduit means having one end adjacent a vapor space that is free of screw windings, the process including the steps of supplying the solid cyanuric chloride along said screw conveyor, compacting the cyanuric chloride to form a gastight stopper of cyanuric chloride at said one end of said conduit means while supplying the cyanuric chloride into said vapor space.

2. The process of claim 1 wherein a gravity operated valve means is provided at said one end of said conduit means and including the step of feeding the cyanuric chloride to said vapor space through said valve means.

* * * * *